United States Patent [19]

Boell et al.

[11] 4,168,379

[45] Sep. 18, 1979

[54] PYRIDIN-3-OLS

[75] Inventors: Walter Boell, Dannstadt-Schauernheim; Horst Koenig, Ludwigshafen, both of Fed. Rep. of Germany

[73] Assignee: BASF Aktiengesellschaft, Fed. Rep. of Germany

[21] Appl. No.: 885,435

[22] Filed: Mar. 10, 1978

[30] Foreign Application Priority Data

Mar. 17, 1977 [DE] Fed. Rep. of Germany ....... 2711656

[51] Int. Cl.$^2$ ................. C07D 221/04; C07D 471/02; C07D 498/04; C07D 213/65
[52] U.S. Cl. ..................................... 546/112; 424/263; 546/113; 546/116; 546/290; 548/235; 548/236; 548/228
[58] Field of Search ........... 260/296 R, 297 R, 297 B, 260/296 B; 424/263; 546/112, 113, 116, 290

[56] References Cited

U.S. PATENT DOCUMENTS

| | | | |
|---|---|---|---|
| 3,227,721 | 1/1966 | Pfister et al. | 260/294.9 |
| 3,227,722 | 1/1966 | Pfister et al. | 260/295.5 |
| 3,227,724 | 1/1966 | Pfister et al. | 260/297 R |
| 3,767,652 | 10/1973 | Wirth | 260/296 D X |

OTHER PUBLICATIONS

Klingsberg, Pyridine and Its Derivatives, Part Three, pp. 766 to 768, Interscience Publishers (1962).
Abramovitch, Pyridine and Its Derivatives, Supplement, Part Three, pp. 670 to 676, Interscience Publication by John Wiley & Sons, (1974).
Daiichi Seyaku Co., Chem. Abstracts, vol. 71, abst. 81203j (abst. of Fr. Pat. 1,530,842), 1969.
Boell et al., Chem. Abstracts, vol. 78, abst. No. 147815p, (1973).
Smirnov et al., Chem. Abstracts, vol. 82, abst. 72747q, (1975).
Zhuravlev et al., Chem. Abstracts, vol. 84, abst. No. 164579f, (1976).

*Primary Examiner*—John D. Randolph
*Attorney, Agent, or Firm*—Keil & Witherspoon

[57] ABSTRACT

New pyridin-3-ols and their N-oxides and acid addition salts, which are useful as intermediates, especially for the preparation of pharmacologically active compounds, and their preparation.

1 Claim, No Drawings

PYRIDIN-3-OLS

The present invention relates to new pyridin-3-ols and their N-oxides and acid addition salts, which are useful as intermediates, especially for the preparation of pharmacologically active compounds, and to their preparation.

We have found that pyridin-3-ols of the general formula I

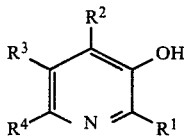

where $R^1$ is hydrogen, alkyl of 1 to 5 carbon atoms, phenylalkyl of 7 to 9 carbon atoms or phenyl, each phenyl ring being unsubstituted or being monosubstituted, disubstituted or trisubstituted by hydroxyl, halogen, e.g. fluorine, chlorine, bromine and iodine, nitro, carboxyl, alkoxycarbonyl or alkoxy, each with alkyl of 1 to 4 carbon atoms, trifluoromethyl or alkyl of 1 to 5 carbon atoms, $R^2$ and $R^3$ may be identical or different and each is hydrogen or alkyl of 1 to 3 carbon atoms which may be unsubstituted or substituted by hydroxyl, halogen, e.g. fluorine, chlorine or bromine, sulfhydryl, alkoxy, alkylthio, amino, monoalkylamino or dialkylamino, where each alkyl is of 1 to 4 carbon atoms, or by acyloxy, where acyl is of 1 to 4 carbon atoms, but at least one of $R^2$ and $R^3$ is not hydrogen, or $R^2$ and $R^3$ together are —CH$_2$—B—CH$_2$—, which forms, with the carbon atoms by which they are linked, a 5-membered to 7-membered ring, and where B is (CH$_2$)$_{1-3}$, oxygen, sulfur,

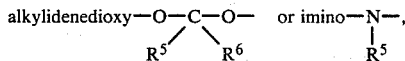

where $R^5$ and $R^6$ are hydrogen, alkyl of 1 to 5 carbon atoms or phenyl, and $R^4$ is phenylalkyl of 7 to 9 carbon atoms or phenyl, each phenyl ring being unsubstituted or being monosubstituted, disubstituted or trisubstituted by hydroxyl, halogen, e.g. fluorine, chlorine, bromine and iodine, nitro, carboxyl, alkoxycarbonyl or alkoxy, each with alkyl of 1 to 4 carbon atoms, trifluoromethyl, alkyl of 1 to 5 carbon atoms or methylenedioxy, or is α-thenyl, and their N-oxides and addition salts with acids are valuable intermediates.

In accordance with the above meanings, if $R^1$ is alkyl of 1 to 5 carbon atoms, it may be a straight-chain or branched radical, e.g. methyl, ethyl, n-propyl, isopropyl, n-butyl, sec.-butyl, isobutyl n-pentyl or isoamyl, whilst if it is phenylalkyl it may be, for example, benzyl or phenylethyl.

If $R^2$ and $R^3$ are alkyl of 1 to 3 carbon atoms they may be, for example, methyl, ethyl or isopropyl whilst if they are substituted alkyl they may be, for example, hydroxymethyl, methoxymethyl, ethoxymethyl, isobutoxymethyl, acetoxymethyl, isobutyroxymethyl, sulfhydrylmethyl, chloromethyl, bromomethyl, methylthiomethyl, dimethylaminomethyl or ethylaminomethyl, and if they conjointly are —CH$_2$—B—CH$_2$— they may be, for example, trimethylene, 2-oxa-trimethylene, 2-thia-trimethylene, or 2-aza-trimethylene, examples of substituents of the nitrogen being methyl, ethyl, isopropyl, isobutyl and phenyl, 2,4-dioxapentamethylene or 3-isopropyl-2,4-dioxapentamethylene.

If $R^4$ is substituted phenyl or phenylalkyl it may be, for example, p-methylphenyl, p-methoxyphenyl, benzyl, m-methylbenzyl, p-methylbenzyl, p-methoxybenzyl, 3,4-dimethoxybenzyl, m-hydroxybenzyl, p-ethoxybenzyl, m-chlorobenzyl, p-chlorobenzyl, p-bromobenzyl, p-fluorobenzyl, o-chlorobenzyl, p-iodobenzyl, α-phenylethyl, α-p-chlorophenylethyl, α-m-methylphenylethyl or β-phenylethyl.

Of the compounds of the formula I, preferred compounds are those where
$R^1$ is hydrogen, alkyl of 1 to 4 carbon atoms, phenyl, benzyl or phenylethyl,
$R^2$ and $R^3$ may be identical or different and are hydrogen or alkyl of 1 to 3 carbon atoms which is substituted by hydroxyl, alkoxy, alkylamino or dialkylamino, each with alkyl of 1 to 4 carbon atoms, by acyloxy, where acyl is of 1 to 4 carbon atoms, or by chlorine or bromine, but at least one of $R^2$ and $R^3$ is not hydrogen, or $R^2$ and $R^3$ together are trimethylene, 2-oxa-trimethylene, azatrimethylene, 2,4-dioxa-pentamethylene, 2-alkyl-2-aza-trimethylene or 3-alkyl-2,4-dioxa-pentamethylene, each with alkyl of 1 to 4 carbon atoms, and
$R^4$ is phenyl, benzyl, α-phenylethyl or β-phenylethyl, phenyl being unsubstituted or monosubstituted or disubstituted by hydroxy, nitro, halogen, alkoxy or alkyl of 1 to 3 carbon atoms, and their N-oxides and addition salts with acids.

Particularly preferred compounds of the formula I are those where
$R^1$ is hydrogen, alkyl of 1 to 4 carbon atoms or benzyl,
$R^2$ and $R^3$ are identical and each is methyl substituted by hydroxyl, alkoxy, alkylamino or dialkylamino, each with alkyl of 1 to 4 carbon atoms, acetoxy, chlorine or bromine, or
$R^2$ and $R^3$ together are trimethylene, 2-oxatrimethylene, 2-aza-trimethylene or 2-alkylazatrimethylene with alkyl of 1 to 4 carbon atoms, and $R^4$ is phenyl or benzyl, where phenyl may be unsubstituted or monosubstituted or disubstituted by hydroxyl, methoxy, halogen, e.g. fluorine, chlorine, bromine or iodine, or methyl.

The new compounds of the formula I may be prepared by reacting an oxazole of the formula II

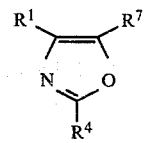

where $R^1$ and $R^4$ have the meanings given for formula I and $R^7$ is hydrogen, alkoxy of 1 to 5 carbon atoms or nitrile, with an olefin of the formula III

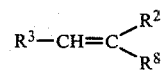

where $R^2$ and $R^3$ have the meanings given for formula I and $R^8$ is hydrogen, alkylsulfonyl of 1 to 5 carbon atoms or phenylsulfonyl, at from 20° to 200° C., with the proviso that at least one of $R^7$ and $R^8$ is hydrogen and that if both $R^7$ and $R^8$ are hydrogen, the reaction is carried out in the presence of a dehydrogenating agent, and, if required, converting the resulting compound by conventional methods to the N-oxide or to an addition salt with an acid.

The above reaction of an oxazole II with an olefin III corresponds to the conventional Diels-Alder reaction and is disclosed in the literature, e.g. Russ. Chem. Rev. 38 (1969), 540–546 or Chemiker-Zeitung 100 (1976), 105–111; it is illustrated by the following equation:

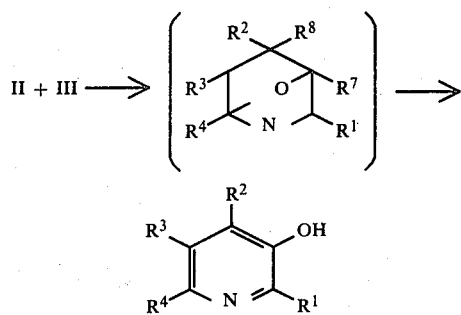

The preferred temperature range is from 50° to 180° C., and the starting compounds are used in a molar ratio of from 1:5 to 5:1. The reaction is advantageously carried out in the absence of a solvent, but in certain cases the excess component may effectively serve as a solvent. Where solvents are used, examples of suitable materials are substituted aromatic or aliphatic hydrocarbons, e.g. nitrobenzene, chlorobenzene, dichlorobenzene, toluene or xylene, aliphatic or cyclic ethers or lower alcohols, e.g. diethyl ether, tetrahydrofuran, 1,2-diethoxyethane, ethanol or methanol, or dimethylformamide or dimethylsulfoxide.

The course of the reaction can easily be followed, for example by thin layer chromatography, and the reaction product is worked up in the conventional manner.

Only in a few cases is the intermediate compound IV, the formula of which is indicated above, observed directly; it is not necessary to isolate this compound, i.e., such isolation has no advantages as far as the preparation is concerned. In many cases, the further reaction of the intermediate to give the pyridin-3-ol (I) takes place spontaneously, with elimination of the radicals $R^7$ and $R^8$.

Preferred starting compounds of the formulae II and III are those where $R^7$ is methoxy, ethoxy, propoxy, isobutoxy or nitrile and $R^8$ is hydrogen, or those where $R^7$ is hydrogen and $R^8$ is methylsulfonyl, ethylsulfonyl, n-butylsulfonyl or phenylsulfonyl, the remaining substituents having the above meanings.

Where both $R^7$ and $R^8$ are hydrogen, the reaction is carried out in the presence of a dehydrogenating agent. Nitrobenzene has proved particularly suitable.

The compounds obtained may or may not be converted into their N-oxides; this conversion may be carried out in the conventional manner, e.g. as disclosed in the literature, Angew. Chemie 70 (1958), 731 et seq.

The oxidizing agent used is hydrogen peroxide, especially in the form of a solution, of from 10 to 50% strength by weight, in water or acetic acid, or in the form of its inorganic or organic derivatives.

Examples of organic derivatives of hydrogen peroxide are per-acids, e.g. peracetic acid, peroxytrifluoroacetic acid, perbenzoic acid, m-chloroperbenzoic acid and monoperphthalic acid, and alkyl hydroperoxides, e.g. tert.-butyl hydroperoxide, whilst an example of an inorganic derivative is peroxydisulfuric acid.

The N-oxidation is advantageously carried out in a solvent, e.g. water or chloroform or, when using peracids, especially in the acids on which these are based, or in mixtures of the said solvents.

In some cases it is advantageous to protect the phenolic hydroxyl group by esterification with an easily removable protective group, advantageously with an acetyl group, before carrying out the N-oxidation.

The oxazoles II used as starting compounds are known compounds or may be prepared without difficulty by processes disclosed in the literature, for example in Chem. Rev. 75 (1975), 389–402, Adv. Heter. Chem. 17 (1974), 99–149, or German Laid-Open Application DOS No. 2,152,367 or DOS 2,451,725.

Examples of oxazoles to be used in accordance with the invention are: 2-phenyl-oxazole, 2-benzyl-oxazole, 2-3'-tolyl-oxazole, 2-3'-trifluoromethylbenzyl-oxazole, 2-3'-anisyl-oxazole, 2-phenyl-4-methyl-oxazole, 2-benzyl-4-methyl-oxazole, 2-benzyl-4-methyl-5-ethoxyoxazole, 2-benzyl-4-methyl-5-cyano-oxazole, 2-3'-methylbenzyl-4-methyl-oxazole, 2-β-phenylethyl-4-methyloxazole, 2-3'-trifluoromethylbenzyl-4-methyl-oxazole, 2-4'-methoxymethyl-phenyl-4-methyl-oxazole, 2-2'-chlorobenzyl-4-methyl-oxazole, 2-3'-chlorophenyl-4-methyl-oxazole, 2-3'-chlorobenzyl-4-methyl-oxazole, 2-3'-chlorobenzyl-4-methyl-5-propoxy-oxazole, 2-4'-chlorobenzyl-4-methyl-oxazole, 2-2',4-dichlorobenzyl-4-methyl-oxazole, 2-3'-fluorobenzyl-4-methyl-oxazole, 2-3'-methoxybenzyl-4-methyl-oxazole, 2-3',4'-dimethoxyphenyl-4-methyl-oxazole, 2-3',4'-dimethoxybenzyl-4-methyloxazole, 2-β-3',4'-methylenedioxyphenylethyl-4-methyl-oxazole, 2-4'-hydroxybenzyl-4-methyloxazole, 2-3',4'-dihydroxybenzyl-4-methyl-oxazole, 2-3'-carboxybenzyl-4-methyl-oxazole, 2-3'-nitrobenzyl-4-methyl-oxazole, 2-benzyl-4-ethyl-oxazole, 2-4'-methylbenzyl-4-ethyl-5-ethoxy-oxazole, 2-3'-bromobenzyl-4-ethyl-5-n-butoxy-oxazole, 2-4'-anisyl-4-ethyloxazole, 2-3',4'-methylenedioxybenzyl-4-ethyl-5-ethoxy-oxazole, 2-2'-chlorobenzyl-4-n-propyl-5-methoxy-oxazole, 2-2'-benzyl-4-isopropyl-5-ethoxyoxazole, 2-β-3'-tolyl-ethyl-4-isopropyl-5-ethoxy-oxazole, 2-(β-4'-anisyl-ethyl)-4-isopropyl-5-ethoxy-oxazole, 2-3'-carbethoxybenzyl-4-isopropyl-5-ethoxy-oxazole, 2-4'-bromophenyl-4-n-butyl-5-methoxy-oxazole, 2-benzyl-4-isobutyl-5-ethoxy-oxazole, 2-4'-ethoxybenzyl-4-n-pentyl-5-ethoxy-oxazole, 2,4-dibenzyl-5-ethoxy-oxazole, 2-4'-nitrobenzyl-4-benzyl-5-ethoxyoxazole and 2-(β-4'-chlorophenylethyl)-4-methyl-oxazole.

Similar remarks apply to the olefins of the formula III, which may be prepared, for example, as described in Synthesis 1971, 563–573, J. Chem. Soc. 1964, 4,962–4,971, J. Org. Chem. 35 (1970), 4,220–4,221 and German Laid-Open Application DOS 2,143,989 or DOS 2,435,098.

Examples of olefins III to be used in accordance with the invention are: 1-methylsulfonyl-but-1-ene, 1-phenylsulfonyl-4-hydroxy-but-1-ene, 1-methylsulfonyl-3-methoxy-prop-1-ene, methyl allyl ether, 1-methylsulfonyl-5-methoxy-pent-1ene, 1-methylsulfonyl-3-hydroxy-but-1-ene, 1-methylsulfonyl-3-acetoxy-prop-1-ene, allyl acetate, 1-phenylsulfonyl-4-acetoxy-but-1-ene, 1-ethylsulfonyl-3-benzoyloxy-prop-1-ene, 3-methylmercapto-prop-1-ene, 1-n-butylsulfonyl-3-dimethylamino-prop-1-ene, 1-methylsulfonyl-3-chloro-prop-1-ene, 1-ethoxy-but-2-ene, but-2-en-1-yl propionate, but-2-ene-1,4-diol, 2-methylsulfonyl-but-2-ene-1,4-diol, 1,4-dimethoxy-but- 2-ene, 2-methylsulfonyl-1,4-dimethoxy-but-2-ene, 1,4-diethoxy-but-2-ene, 2-methylsulfonyl-1,4-dimethoxy-but-2-ene, 1,4-diacetoxy-but-2-ene, 1,4-dimethylmercapto-but-2-ene, 1,4-dichloro-but-2-ene, 1,4-difluoro-but-2-ene, 1-methylsulfonyl-cyclopentene, 1-ethylsulfonylcyclohexene, 1-methylsulfonyl-cycloheptane, 2,5-dihydrofuran, 3-methylsulfonyl-2,5-dihydrofuran, 3-phenylsulfonyl-2,5-dihydrofuran, 2,5-dihydrothiophene, 3-methylsulfonyl-2,5-dihydrothiophene, 4,7-dihydro-1,3-dioxepine, 2,2-dimethyl-4,7-dihydro-1,3-dioxepine, 2-isopropyl-4,7-dihydro-1,3-dioxepine and 2-phenyl-4,7-dihydro-1,3-dioxepine.

Some of the pyridin-3-ols of the formula I can also be prepared advantageously by reacting a pyridinol I, where $R^2$ and $R^3$ together are 2-oxatrimethylene, in an ether scission with hydrogen chloride in water or glacial acetic acid at from 100° to 160° C. under a pressure of from 10 to 50 bars, or with azeotropically boiling hydrobromic acid under atmospheric pressure, the corresponding di-(halomethyl) compounds being obtained which in turn are starting compounds for the di-(hydroxymethyl), di-(alkoxymethyl) or di-(alkylaminomethyl) compounds or 2,3-dihydro-1H-pyrrolo[3,4-c]pyridin-7-ols.

The mono-(halomethyl), mono-(alkoxymethyl) and mono-(alkylaminomethyl) compounds can be obtained by a similar method, and the latter is also obtainable by a Mannich reaction.

The compounds according to the invention can be converted in the conventional manner to the addition salts with acids, especially with strong inorganic acids, e.g. hydrohalic acids, e.g. hydrogen chloride or hydrogen bromide, sulfuric acid or phosphoric acid, or with organic acids, e.g. sulfonic acids.

The pyridin-3-ols of the invention are valuable intermediates for the preparation of pharmacologically active compounds, and in particular, aminoalkyl ethers of the formula V derived from these intermediates have a powerful antiarrhythmic and/or local anaesthetic action.

Compounds of the formula V

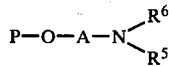

where P-O is the pyridinol radical of the formula I and A in particular is alkylene of 3 to 5 carbon atoms, which may or may not be substituted by methyl, or is 2-hydroxy-1,3-propylene, and $R^5$ is hydrogen or alkyl of 1 to 5 carbon atoms, which may or may not be substituted by hydroxyl, or is benzyl, and $R^6$ is hydrogen or alkyl of 1 to 4 carbon atoms, or $R^5$ and $R^6$ together with the nitrogen atom are a pyrrolidone, piperidine or piperazine ring, and their physiologically acceptable addition salts with acids may be prepared, for example, by reacting a pyridinol of the general formula I or its N-oxide with an alkylating agent of the general formula

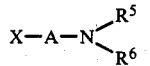

where X is a reactive esterified hydroxyl group and A, $R^5$ and $R^6$ have the abovementioned meanings, advantageously in a solvent and in the presence of a base, if appropriate using the phase transfer method, and then, if required, converting the product into the addition salt with a physiologically acceptable acid.

A reaction esterified hydroxyl group X is in particular a hydroxyl group esterified by a strong inorganic or organic acid, above all a hydrohalic acid, e.g. hydrochloric acid, hydrobromic acid or hydriodic acid, sulfuric acid or a strong organic sulfonic acid, e.g. benzenesulfonic acid, methanesulfonic acid or 4-toluenesulfonic acid. Preferably, X is chlorine, bromine or iodine.

The reaction is advantageously carried out in the presence of an equivalent or excess amount of a base as an acid-binding agent, examples of such bases being the alkali metal hydroxides, carbonates or alcoholates, amongst which the sodium and potassium compounds are preferred.

The reaction may also be carried out with the starting compound of the formula I in the form of its alkali metal salt, especially the sodium salt or potassium salt, which may be obtained directly from the P-OH of the formula I. The salts are formed by reaction with the above alkali metal compounds or, especially if an aprotic solvent is used, with sodium or potassium amide or hydride.

The reaction is advantageously carried out in a solvent at from 0° to 150° C., preferably from 20° to 100° C. Advantageous solvents are lower alcohols of 1 to 4 carbon atoms, especially methanol and ethanol, lower aliphatic ketones, especially acetone, benzene, alkylbenzenes and halobenzenes, e.g. chlorobenzene and toluene, aliphatic and cyclic ethers, e.g. diethyl ether, tetrahydrofuran and dioxane, dimethylformamide and dimethylsulfoxide. If an ether is to be used as the solvent, hexamethylphosphorotriamide may advantageously be added thereto as an additional solvent.

In an advantageous embodiment, especially if the pyridinol does not contain any readily hydrolyzable functional groups, two-phase solvent mixtures, especially mixtures of water with a chlorohydrocarbon, e.g. methylene chloride, or with a benzene hydrocarbon, e.g. benzene or toluene, are used, employing the conventional method of phase transfer catalysis as described, for example, by M. Makosza in Pure and Applied Chemistry, 1975, No. 43, page 439. The preferred bases to use are mixtures of an alkali metal hydroxide, especially sodium hydroxide, with a quaternary ammonium base or a phosphonium base, which second constituent is employed in a catalytic amount, in the form of its salt, e.g. triethylbenzylammonium chloride, tetrabutylammonium bisulfate or tributylhexadecyl-phosphonium bromide.

The compounds of the formula V can also be obtained by reacting a pyridinol of the general formula I, or its N-oxide, with a compound of the general formula X-A-Y, where X and Y are reactive esterified hydroxyl groups, especially chlorine, bromine or iodine, advantageously in a solvent, and in the presence of a base as the acid-binding agent, and then reacting the resulting compound of the general formula VI

 VI with an amine of the formula $R^5$-NH-$R^6$, where $R^5$ and $R^6$ have the abovementioned meanings, and, if desired, converting the end product into its addition salt with a physiologically acceptable acid.

The process conditions for the preparation of the intermediate of the formula VI correspond to those of the above process in respect of the solvents used, the bases employed as acid-binding agents, and the temperatures. In order to minimize the formation of by-products, especially to minimize etherification reactions with 2 moles of P-OH, X-A-Y is advantageously employed in at least a two-fold molar excess, or a compound where X and Y are advantageously different is used, so that the different reactivity of these groups can be utilized, as is the case, for example, if one is bromine and the other is chlorine.

The intermediate of the formula III may be isolated and then reacted, by itself, with an amine $R^5$-NH-$R^6$, or may be reacted with the amine directly in the reaction mixture obtained from the first process step.

This reaction is also carried out as described above, advantageously in a solvent and in the presence of a base. An excess of the amine $R^5$-NH-$R^6$ may also be used as the base, and can at the same time serve as a solvent. The reaction is carried out at elevated temperatures, in general at from 60° to 120° C., under atmospheric pressure or, if appropriate, in a closed vessel inder superatmospheric pressure, especially if a volatile amine is used.

Attention is drawn to the fact that aminoalkyl ethers of the formula V, their preparation and their use as medicaments form the subject matter of co-pending German Patent Application P 27 11 655.8, having the same date of filing.

EXAMPLE 1
1-Benzyl-3-methyl-6,7-dihydro-5H-2-pyridin-4-ol

A mixture of 14.6 g (100 millimoles) of 1-methyl-sulfonyl-cyclopentene and 34.6 g (200 millimoles) of 2-benzyl-4-methyl-oxazole is heated for 2 days at 180° C. It is then taken up in 200 ml of methylene chloride, and the insoluble constituent is filtered off and suspended in 75 ml of 1 N hydrochloric acid. The aqueous solution is concentrated to dryness and the residue is recrystallized from water. 6.9 g of 1-benzyl-3-methyl-6,7-dihydro-5H-2-pyridin-4-ol hydrochloride, melting point 104°-106° C., are obtained.

| C, H and N determination ($C_{16}H_{18}ClNO$; 275.5) | | | |
| --- | --- | --- | --- |
| Found: | C 64.7%; | H 6.5%; | N 5.1% |
| Calculated: | 65.1 | 6.9 | 5.0 |

EXAMPLE 2
4-Phenyl-6-methyl-1,3-dihydro-furo[3,4-c]pyridin-7-ol

A mixture of 22.5 g (150 millimoles) of 3-methylsulfonyl-2,5-dihydrofuran and 24 g (150 millimoles) of 2-phenyl-4-methyloxazole is heated for 16 hours at 160° C. The unconverted oxazole is distilled off in a high vacuum and the residue is chromatographed over silica gel using ethyl acetate. The eluate is converted to the hydrochloride by heating in dilute hydrochloric acid and is recrystallized from water. 13.5 g of 4-phenyl-6-methyl-1,3-dihydro-furo[3,4-c]pyridin-7-ol hydrochloride, of melting point 248°-251° C., are obtained.

| C, H and N determination ($C_{14}H_{14}ClNO_2$; 263.5) | | | |
| --- | --- | --- | --- |
| Found: | C 63.4%; | H 5.5%; | N 5.2% |
| Calculated: | 63.7 | 5.3 | 5.3 |

EXAMPLE 3
4-Benzyl-6-methyl-1,3-dihydro-furo[3,4-c]pyridin-7-ol

A mixture of 296 g (2 moles) of 3-methylsulfonyl-2,5-dihydrofuran and 692 g (4 moles) of 2-benzyl-4-methyloxazole is heated for 20 hours at 150° C. When the mixture has cooled, it is suspended in 1 l of methylene chloride. The solution contains unconverted oxazole. The undissolved constituent is a mixture of 4-benzyl-6-methyl-1,3-dihydro-furo[3,4-c]pyridin-7-ol and 3,4-dimethylsulfonyl-tetrahydrofuran, which is separated by digesting in 1.35 l of nitromethane. 186 g of 4-benzyl-6-methyl-1,3-dihydro-furo[3,4-c]pyridin-7-ol, of melting point 212°-214° C., remain undissolved. After recrystallization from methanol, the melting point is 215° C.

| C, H and N determination ($C_{15}H_{15}NO_2$; 241) | | | |
| --- | --- | --- | --- |
| Found: | C 74.4%; | H 6.2%; | N 6.2% |
| Calculated: | 74.7 | 6.2 | 5.8 |

The hydrochloride melts at 251° C. after recrystallization from water.

The reaction can also be carried out with 3-ethyl-sulfonyl-2,5-dihydrofuran or 3-phenylsulfonyl-2,5-dihydrofuran.

EXAMPLE 4
2-Methyl-4,5-di-(chloromethyl)-6-benzyl-pyridin-3-ol 25 g of 4-benzyl-6-methyl-1,3-dihydro-furo[3,4-c]pyridin-7-ol (Example 3) in 80 ml of glacial acetic acid are heated under a hydrogen chloride pressure of 40-45 bars in a tantalum autoclave for 8 hours at 140° C. After distilling off the glacial acetic acid, the residue is suspended in 100 ml of acetone. On concentrating the solution, 27 g of crude 2-methyl-4,5-di-(chloromethyl)-6-benzyl-pyridin-3-ol hydrochloride are obtained.

The compound can advantageously be purified by converting it to the acetate ester by heating with acetic anhydride in glacial acetic acid for 2 hours at 100° C. After distilling off the solvent, the residue is recrystallized from ethyl acetate. 2-Methyl-4,5-di-(chloromethyl)-6-benzyl-pyridin-3-yl acetate hydrochloride, of melting point 143°-144° C., is obtained.

| C, H and N determination ($C_{17}H_{18}Cl_3NO_2$; 374.5) | | | |
| --- | --- | --- | --- |
| Found: | C 54.0%; | H 4.5%; | N 3.7% |
| Calculated: | 54.5 | 4.8 | 3.7 |

EXAMPLE 5
2-Methyl-4,5-di-(hydroxymethyl)-6-benzyl-pyridin-3-ol

A solution of 20 g of crude 2-methyl-4,5-di-(chloromethyl)-6-benzyl-pyridin-3-ol in 40 g of 75% strength formic acid is heated under reflux. After 10 minutes, a solution of 10.7 g of sodium hydroxide in 15 ml of water is added and heating is continued for 1 hour. The mixture is concentrated to dryness under reduced pressure. The residue is digested in 100 ml of acetone, the insoluble constituent is filtered off, the filtrate is concentrated and the residue thus obtained is boiled for ½ hour in 50 ml of water. After again concentrating the mixture, the residue is recrystallized from acetone. 5.7 g of 2-methyl-4,5-di-(hydroxymethyl)-6-benzyl-pyridin-3-ol, of melting point 158°–159° C., are obtained.

| C, H and N determination (C$_{15}$H$_{17}$NO$_3$; 259) | | | |
|---|---|---|---|
| Found: | C 69.1%; | H 6.7%; | N 5.4% |
| Calculated: | 69.5 | 6.6 | 5.4 |

EXAMPLE 6

2-Methyl-4,5-di-(methoxymethyl)-6-benzyl-pyridin-3-ol

A mixture of 19.4 g (0.1 mole) of 2-methylsulfonyl-1,4-dimethoxy-but-2-ene and 34.6 g (0.2 mole) of 2-benzyl-4-methyloxazole is heated for 10 hours at 190° C. After it has cooled, unconverted oxazole and sulfone are distilled off in a high vacuum. The residue is chromatographed over silica gel (using ethyl acetate and methanol). 5.5 g of 2-methyl-4,5-di-(methoxymethyl)-6-benzyl-pyridin-3-ol, identified by the NMR spectrum, are obtained.

The same compound is obtained in a yield of about 75% from 2-methyl-4,5-di-(chloromethyl)-6-benzyl-pyridin-3-yl acetate hydrochloride by heating in methanol at 150° C. in an autoclave for 5 hours and then chromatographing the crude product over silica gel.

NMR spectrum (60 Mc/s in CDCl$_3$): singlets at 2.35 (3), 3.0 (3), 3.3 (3), 4.05 (2), 4.15 (2), 4.6 (2) and 6.95 ppm (5 protons).

EXAMPLE 7

2,6-Dimethyl-4-benzyl-2,3-dihydro-1H-pyrrolo[3,4-c]pyridin-7-ol

A mixture of 37.5 g (100 millimoles) of 2-methyl-4,5-di-(chloromethyl)-6-benzyl-pyridin-3-yl acetate hydrochloride (Example 4), 50 ml of dry dimethylsulfoxide and 16 g (500 millimoles) of methylamine is heated for 5 hours at 80° C. in an autoclave. The solvent is stripped off in a high vacuum and the residue is partitioned between methylene chloride and water, taking care that the pH of the aqueous phase is 7.

The methylene chloride phase is evaporated to dryness. On digesting the residue with ethyl acetate, 11.5 g of 2,6-dimethyl-4-benzyl-2,3-dihydro-1H-pyrrolo[3,4-c]pyridin-7-ol, of melting point 195° C., are obtained.

Further product is obtained by concentrating the ethyl acetate phase and then chromatographing over silica gel (using ethyl acetate and methanol). The product is purified by recrystallization from isopropanol.

NMR spectrum (60 Mc/s, DDMSO); δ=2.3 ppm, (s, C-CH$_3$); 2.4 ppm (s, N-CH$_3$); 3.7 ppm (broad, N-CH$_2$); 3.85 ppm (s, C-CH$_2$); 7.1 ppm (s, aromatic).

EXAMPLES 8 AND 9

2-Methyl-4-methoxymethyl-6-benzyl-pyridin-3-ol and 2-methyl-5-methoxymethyl-6-benzyl-pyridin-3-ol (a) 1-Methylsulfonyl-3-methoxy-prop-1-ene 159 g (1 mole) of methanesulfonyl bromide are slowly added dropwise, at 45° C., to a mixture of 78 g (1.07 moles) of methyl allyl ether, 7.5 g of zinc chloride and 3.3 ml of 50% strength hydrogen peroxide. After the exothermic reaction has subsided, the mixture is stirred for a further 30 minutes and is diluted with 450 ml of benzene, and 135 g (1.33 moles) of triethylamine are added at room temperature, whilst cooling. After 2 hours, the precipitate is filtered off and the solvent is distilled off. Distillation of the residue gives 125 g of 1-methylsulfonyl-3-methoxy-prop-1-ene, boiling point 114°–115° C./0.3 mm Hg. According to the NMR spectrum, the product is a mixture of cis and trans isomers in the ratio of 15:85.

(b) A mixture of 75 g (0.5 mole) of 1-methylsulfonyl-3-methoxy-prop-1-ene and 173 g (1 mole) of 2-benzyl-4-methyloxazole is heated for 8 hours at 150° C. The unconverted oxazole is distilled off in a high vacuum, the residue is taken up in methylene chloride and the solution is extracted twice with 150 ml of 10% strength sodium hydroxide solution. The alkaline phase is neutralized with hydrochloric acid and extracted with methylene chloride. After distilling off the solvent, 66.6 g of a mixture of 2-methyl-4- and 5-methoxymethyl-6-benzyl-pyridin-3-ol, in the ratio of 1:3 according to the NMR spectrum, remain.

The product is separated and purified by column chromatography over silica gel (using methylene chloride and ethyl acetate) and subsequent recrystallization from isopropanol).

2-Methyl-4-methoxymethyl-6-benzyl-pyridin-3-ol, A

Melting point 172°–173° C. (recrystallization from nitromethane)    2-Methyl-5-methoxymethyl-6-benzyl-pyridin-3-ol, B Melting point 99°–100° C. (recrystallization from isopropanol)

| NMR spectra (60 Mc/s, CDCl$_3$): | | | | | |
|---|---|---|---|---|---|
| A | CH$_3$O 3.05; | CH$_2$O 4.0; | =C—H | 6.8 ppm | |
| B | 3.35 | 4.45 | | 6.45 | |
| C, H and N determination (C$_{14}$H$_{17}$NO$_2$; 231) | | | | | |
| A found: | C 72.5%; | H 7.2%; | N 6.0% | | |
| B found: | 72.7 | 7.5 | 6.1 | | |
| Calculated | 72.7 | 7.4 | 6.1 | | |

EXAMPLES 10

2-Methyl-4-dimethylaminomethyl-6-benzyl-pyridin-3-ol

This compound is prepared from 2-methyl-4-methoxymethyl-6-benzyl-pyridin-3-ol via 2-methyl-4-chloromethyl-6-benzyl-pyridin-3-ol obtainable by ether splitting as described in Example 4, by reaction with dimethylamine.

A more advantageous method is a Mannich reaction starting from 2-methyl-6-benzyl-pyridin-3-ol N-oxide, giving the N-oxide of the end product:

A mixture of 8.6 g (40 millimoles) of 2-methyl-6-benzyl-pyridin-3-ol N-oxide, 5 g of 30% strength aqueous formaldehyde solution, 5.5 g of 40% strength aqueous dimethylamine solution and 9 ml of water is heated for 2 hours at 80° C. It is then evaporated to dryness, the residue is taken up in chloroform, this solution is shaken with active charcoal and filtered, and the solvent is distilled off. 10.2 g of 2-methyl-4-dimethylaminomethyl-6-benzyl-3-pyridin-3-ol N-oxide remain.

| NMR spectrum (60 Mc/s, CDCl$_3$): | | | | | |
|---|---|---|---|---|---|
| N(CH$_3$)$_2$ | C—CH$_3$ | N—CH$_2$ | C—CH$_2$ | =C—H | C$_6$H$_5$ |
| 2.25 | 2.58 | 3.48 | 4.1 | 6.3 | 7.13 ppm |
| C, H and N determination (C$_{16}$H$_{20}$N$_2$O$_2$; 272) | | | | | |
| Found/ | C 70.3%; | H 7.5%; | N 10.1%; | | |
| Calculated: | 70.6 | 7.4 | 10.3 | | |

EXAMPLE 11

6-Benzyl-8-methyl-1,5-dihydro[1,3]dioxepino[5,6-c]pyridin-9-ol (a) 2-Benzyl-4-methyl-5-ethoxyoxazole A solution of 117.5 g (0.5 mole) of N-phenylacetyl-α-alanine ethyl ester in 250 ml of chloroform is added dropwise, at 20° C., to a vigorously stirred mixture of 123 g of magnesium oxide, 600 g of phosphorus pentoxide (75% strength on a carrier) and 2.5 l of chloroform. The mixture is refluxed for 4 hours and then carefully introduced into 2 l of ice water, the batch is brought to pH 9 by adding dilute sodium hydroxide solution and the precipitate is filtered off. The chloroform phase is separated from the aqueous phase and concentrated under reduced pressure. Distillation of the residue gives 38 g of 2-benzyl-4-methyl-5-ethoxyoxazole, boiling point 120°–126°/0.4 mm Hg; $n_D^{20}$ 1.517.

(b) A mixture of 8.4 g (40 millimoles) of 2-benzyl-4-methyl-5-ethoxyoxazole and 20 g (200 millimoles) of 4,7-dihydro-1,3-dioxepine is heated for 4 hours at 180° C. in an autoclave. Unconverted 4,7-dihydro-1,3-dioxepine is distilled off under reduced pressure. The residue is taken up in methylene chloride and extracted with 10% strength sodium hydroxide solution. On neutralizing the alkaline solution, 5.2 g of 6-benzyl-8-methyl-1,5-dihydro-[1,3]dioxepino[5,6-c]pyridin-9-ol precipitate and these are extracted with methylene chloride.

The product is purified by chromatography over silica gel (using ethyl acetate and methanol), converted to the hydrochloride and recrystallized from isopropanol.

Melting point 213–214° C.
C, H and N determination ($C_{16}H_{18}ClNO_3$; 307.5)

|  | C | H | N |
|---|---|---|---|
| Found: | 62.3%; | 6.1%; | 4.6% |
| Calculated: | 62.4 | 5.9 | 4.5 |

EXAMPLE 12

3-Isopropyl-6-benzyl-8-methyl-1,5-dihydro-[1,3]dioxepino[5,6-c]pyridin-9-ol

A mixture of 12.6 g (60 millimoles) of 2-benzyl-4-methyl-5-ethoxy-oxazole and 42.6 g (300 millimoles) of 2-isopropyl-4,7-dihydro-1,3-dioxepine is heated for 5 hours at 180° C. On cooling the mixture in an ice bath, 4.2 g of 3-isopropyl-6-benzyl-8-methyl-1,5-dihydro-[1,3]dioxepino[5,6-c]pyridin-9-ol crystallize out. A further 2.0 are obtained by evaporating the mother liquor, partitioning the residue between methylene chloride and dilute sodium hydroxide solution and neutralizing the alkaline phase. Recrystallization from ethyl acetate gives a pure product, of melting point 193°–194° C.

C, H and N determination ($C_{19}H_{23}NO_3$; 313)

|  | C | H | N |
|---|---|---|---|
| Found: | 72.5%; | 7.2%; | 4.5% |
| Calculated: | 72.6 | 7.3 | 4.5 |

EXAMPLE 13

4-β-Phenylethyl-6-methyl-1,3-dihydro-furo[3,4-c]pyridin-7-ol 18.7 g (100 millimoles) of 2-β-phenylethyl-4-methyloxazole and 29.6 g (200 millimoles) of 3-methylsulfonyl-2,5-dihydrofuran are heated at 160° C. for 20 hours. The mixture is digested in methylene chloride and the residue is filtered off, digested in nitromethane and again filtered off. 10.5 g are obtained. Subsequent recrystallization from dimethylformamide gives pure 4-β-phenylethyl-6-methyl-1,3-dihydro-furo[3,4-c]pyridin-7-ol of melting point 248° C.

C, H and N determination ($C_{16}H_{17}NO_2$; 255)

|  | C | H | N |
|---|---|---|---|
| Found: | 75.3%; | 6.6%; | 5.4% |
| Calculated: | 75.3 | 6.7 | 5.5 |

EXAMPLE 14

4-3'-Methylbenzyl-6-methyl-1,3-dihydro-furo[3,4-c]pyridin-7-ol (a) 2-3'-Methyl-benzyl-4-methyl-oxazole 220 g of 3-methylphenylacetimido-propargyl ester are added dropwise to 10 g of silver tosylate at 100°–110° C. The mixture is then distilled to give 160 g of 2-3'-methylbenzyl-4-methyl-oxazole, of boiling point 95°/0.1 mm Hg.

(b) 93.5 g (0.5 mole) of 2-3'-methylbenzyl-4-methyl-oxazole and 74.0 g (0.5 mole) of 3-methylsulfonyl-2,5-dihydrofuran are heated at 150° C. for 20 hours. The mixture is worked up as described in Example 13. 32 g of 4-3'-methylbenzyl-6-methyl-1,3-dihydro-furo[3,4-c]pyridin-7-ol are obtained; melting point, after recrystallization from methanol, 207°–208° C.

C, H and N determination ($C_{16}H_{17}NO_2$; 255)

|  | C | H | N |
|---|---|---|---|
| Found: | 75.3%; | 6.7%; | 5.6% |
| Calculated: | 75.3 | 6.7 | 5.5 |

EXAMPLE 15

4-4'-Chlorobenzyl-6-methyl-1,4-dihydro-furo[3,4-c]pyridin-7-ol (a) 2-4'-Chlorobenzyl-4-methyloxazole 112 g of 4-chlorophenylacetimido-propargyl ester are added dropwise, at 110°–120° C., to a suspension of 5 g of silver tosylate in 5 ml of xylene. The subsequent distillation gives 93 g of 2-4'-chlorobenzyl-4-methyloxazole, of boiling point 110°/0.1 mm Hg.

(b) Using the method of Example 14, 104 g of 2-4'-chlorobenzyl-4-methyloxazole and 74 g of 3-methylsulfonyl-2,5-dihydrofuran are reacted to give 37.5 g of 4-4'-chlorobenzyl-6-methyl-1,3-dihydro-furo[3,4-c]pyridin-7-ol. After recrystallization from methanol the melting point is 221°–222° C.

C, H and N determination ($C_{15}H_{14}ClNO_2$; 275.5)

|  | C | H | N |
|---|---|---|---|
| Found: | 65.4%; | 5.3%; | 5.0% |
| Calculated: | 65.4 | 5.1 | 5.1 |

EXAMPLE 16

4-3'-Chlorobenzyl-6-methyl-1,3-dihydro-furo[3,4-c]pyridin-7-ol (a) 2-3'-Chlorobenzyl-4-methyloxazole 83 g of 3-chlorophenylacetimidopropargyl ester are added dropwise, at 110°–120° C., to a suspension of 4 g of silver tosylate in 5 ml of xylene. The subsequent distillation gives 67 g of 2-3'-chlorobenzyl-4-methyloxazole, of boiling point 110°–112°/0.05 mm Hg.

(b) Using the method of Example 14, 104 g of 2-3'-chlorobenzyl-4-methyloxazole and 74 g of 3-methylsulfonyl-2,5-dihydrofuran are reacted to give 36 g of 3-methylsulfonyl-6-methyl-1,3-dihydro-furo[3,4-c]pyridin-7-ol. After recrystallization from methanol the melting point is 205°–206° C.

| C, H and N determination ($C_{15}H_{14}ClNO_2$; 275.5) | | | |
|---|---|---|---|
| Found: | C 65.4%; | H 5.1%; | N 5.1% |
| Calculated: | 65.4 | 5.1 | 5.1 |

EXAMPLE 17

4-4'-Nitrobenzyl-6-methyl-1,3-dihydro-furo[3,4-c]pyridin-7-ol (a) 2-4'-Nitrobenzyl-4-methyloxazole is prepared from p-nitrophenylacetimido-propargyl ester by a method similar to the preparation of 2-benzyl-4-methyloxazole described in German Laid-Open Application DOS 2,152,367; its melting point is 65°–66° (after recrystallization from isopropanol).

(b) Using the method of Example 14, 109 g of 2-4'-nitrobenzyl-4-methyloxazole and 74 g of 3-methylsulfonyl-2,5-dihydrofuran are reacted to give 38 g of 4-4'-nitrobenzyl-6-methyl-1,3-dihydro-furo[3,4-c]pyridin-7-ol. After recrystallization from acetone the melting point is 225°–227° C.

| C, H and N determination ($C_{15}H_{14}N_2O_4$; 286) | | | |
|---|---|---|---|
| Found: | C 62.7%; | H 5.0%; | N 10.0% |
| Calculated: | 62.9 | 4.9 | 9.8 |

EXAMPLE 18

4-3'-4'-Dimethoxyphenyl-6-methyl-1,3-dihydro-furo[3,4-c]pyridin-7-ol (a) 2-3',4'-Dimethoxyphenyl-4-methyloxazole 23 g of 3,4-dimethoxy-benzimido-propargyl ester (obtained from 3,4-dimethoxy-benzonitrile by a Pinner reaction) are added in portions to 1 g of silver tosylate at 110°–120° C. Subsequent distillation gives 19.5 g of 2-3',4'-dimethoxyphenyl-4-methyloxazole, boiling point about 130°/0.1 mm Hg. After recrystallization from ether, the melting point is 91°–93° C.

| C, H and N determination ($C_{12}H_{13}NO_3$; 219) | | | |
|---|---|---|---|
| Found: | C 65.9%; | H 6.0%; | N 6.5% |
| Calculated: | 65.8 | 6.0 | 6.4 |

(b) 22 g (100 millimoles) of 2-3',4'-dimethoxyphenyl-4-methyloxazole and 14.8 g (100 millimoles) of 3-methylsulfonyl-2,5-dihydrofuran are heated for 80 hours at 130° C. The unconverted starting compounds are distilled off in a high vacuum. On digesting the distillation residue with nitromethane, 6.5 g of 4-3',4'-dimethoxyphenyl-6-methyl-1,3-dihydro-furo[3,4-c]pyridin-7-ol remain undissolved. This material is recrystallized from methanol; melting point 185°–186° C.

| C, H and N determination ($C_{16}H_{17}NO_4$; 287) | | | |
|---|---|---|---|
| Found: | C 66.4%; | H 6.3%; | N 4.8% |
| Calculated: | 66.9 | 5.9 | 4.9 |

EXAMPLE 19

4-3',4'-Dimethoxybenzyl-6-methyl-1,3-dihydro-furo[3,4-c]pyridin-7-ol (a) 2-3',4'-Dimethoxybenzyl-4-methyloxazole is prepared by a method similar to Example 18, starting from 3,4-dimethoxyphenylacetonitrile, boiling point 125°–127°/0.01 mm Hg.

| C, H and N determination ($C_{13}H_{15}NO_3$; 223) | | | |
|---|---|---|---|
| Found: | C 67.1%; | H 6.7%; | N 5.6% |
| Calculated: | 66.9 | 6.4 | 6.0 |

(b) 35 g (150 millimoles) of 2-3',4'-dimethoxybenzyl-4-methyloxazole and 22.2 g (150 millimoles) of 3-methylsulfonyl-2,5-dihydrofuran are heated for 13 hours at 170° C. The mixture is digested in ethanol and the residue is filtered off, digested in 150 ml of nitromethane and again filtered off. 13.5 g of 4-3',4'-dimethoxybenzyl-6-methyl-1,2-dihydro-furo[3,4-c]pyridin-7-ol are left, melting point 233° C.

The hydrochloride, melting point 205° C., is obtained by dissolving the material in dilute hydrochloric acid and evaporating the solution.

| C, H and N determination ($C_{17}H_{20}ClNO_4$; 337.5) | | | |
|---|---|---|---|
| Found: | C 60.2% | H 5.9%; | N 4.2% |
| Calculated: | 60.5 | 5.6 | 4.2 |

EXAMPLE 20

4-Benzyl-1,3-dihydro-furo[3,4-c]pyridin-7-ol (a) 2-Benzyloxazole

A solution of 197 g (1.4 moles) of glycine ethyl ester hydrochloride in 230 ml of water and a solution of 228 g of phenylacetimido-ethyl ester in 100 ml of ether are stirred for 2.5 hours at −10° C. and 15 hours at 0° C. The ether phase is separated off, the aqueous phase is extracted with four times 100 ml of ether, the combined ether solutions are evaporated and the residue is distilled. 58 g of N-carbethoxymethylphenylacetimido-ethyl ester are obtained.

A mixture of this ester with 17.5 g of ethyl formate is added dropwise at −5° C. to potassium ethylate (prepared from 9.2 g of potassium and 33 g of ethanol) in 500 ml of absolute ether. After 15 hours, the ether is distilled off and the residue is introduced into 140 ml of boiling glacial acetic acid. The glacial acetic acid is distilled off under reduced pressure and the residue is partitioned between methylene chloride and water. Distillation gives 28.5 g of ethyl 2-benzyloxazole-4-carboxylate, boiling point 144°/0.1 mm Hg.

Hydrolysis of this ester with a solution of sodium hydroxide in methanol at 15° C. gives 20.5 of 2-benzyloxazole-4-carboxylic acid, melting point 155°–156° C., which, when decarboxylated with copper powder at 210°–220° C., gives 12.5 g of 2-benzyloxazole, boiling point 134°–136°/25 mm Hg; $n_D^{25}$ 1.5395.

| C, H and N determination (C$_{10}$H$_9$NO; 159) | | | |
|---|---|---|---|
| Found: | C 75.6%; | H 5.7%; | N 9.1% |
| Calculated: | 75.5 | 5.7 | 8.8 |

(b) 11.2 g (70 millimoles) of 2-benzyloxazole and 10.5 g (70 millimoles) of 3-methylsulfonyl-2,5-dihydrofuran are heated for 7 hours at 160°. The unconverted starting compounds are distilled off in a high vacuum and the distillation residue is extracted with methylene chloride. The 4-benzyl-1,3-dihydro-furo[3,4-c]pyridin-7-ol contained in the extract is separated off by chromatography over silica gel (using methylene chloride and ethyl acetate). 4.3 g are obtained. Recrystallization from benzene/methylene chloride gives a pure product.

NMR spectrum (60 Mc/s, DDMSO):
C—CH$_2$   O—CH$_2$   C$_6$H$_5$   =C—H
3.9   4.9   7.5   7.9 ppm (singlets)

| C, H and N determination (C$_{14}$H$_{13}$NO$_2$; 227) | | | |
|---|---|---|---|
| Found: | C 73.8%; | H 5.5%; | N 6.3% |
| Calculated: | 74.0 | 5.7 | 6.2 |

EXAMPLE 21

4-Benzyl-6-ethyl-1,3-dihydro-furo[3,4-c]pyridin-7-ol (a) 2-Benzyl-4-ethyloxazole 128 g (0.5 mole) of phenylacetimido-cyclohexyl ester hydrochloride are introduced, at room temperature, into a mixture of 23 g (0.25 mole) of 2-ketobutanol and 100 g of N,N-dimethylaniline. The mixture is heated for 2.5 hours at 100° C., after cooling 250 ml of 10% strength sodium hydroxide solution are added, and the whole is extracted with methylene chloride. After distilling off the solvent, the residue is subjected to fractional distillation. 9.5 g of 2-benzyl-4-ethyloxazole, boiling point 74°–76°/0.2 mm Hg, are obtained.

(b) 9.4 g (50 millimoles) of 2-benzyl-4-ethyloxazole and 29.6 g. (200 millimoles) of 3-methylsulfonyl-2,5-dihydrofuran are heated for 15 hours at 150°. Unconverted sulfone is distilled off in a high vacuum. The residue is digested in methylene chloride, the undissolved constituent is filtered off, and the filtrate is extracted with 150 ml of 10% strength sodium hydroxide solution. The alkaline solution is neutralized and extracted with methylene chloride. On concentrating the methylene chloride solution, 6.2 g of 4-benzyl-6-ethyl-1,3-dihydro-furo[3,4-c]pyridine-7-ol remain. Melting point, after recrystallization from nitromethane: 148° C.

| C, H and N determination (C$_{16}$H$_{17}$NO$_2$; 255) | | | |
|---|---|---|---|
| Found: | C 75.2%; | H 6.7%; | N 5.6% |
| Calculated: | 75.3 | 6.7 | 5.5 |

EXAMPLE 22

4-Benzyl-6-isopropyl-1,3-dihydro-furo[3,4-c]pyridin7-ol (a) 2-Benzyl-4-isopropyl-5-ethoxyoxazole is prepared by a method similar to Example 11 (a). 131.5 g of N-phenylacetyl-valine ethyl ester give, after distillation of the product, 77 g oxazole, boiling point 115°/0.1 mm Hg.

| C, H and N determination (C$_{15}$H$_{19}$NO$_2$; 245) | | | |
|---|---|---|---|
| Found: | C 73.2%; | H 7.8%; | N 6.1% |
| Calculated: | 73.5 | 7.8 | 5.7 |

(b) 36.8 g of 2-benzyl-4-isopropyl-5-ethoxyoxazole (150 millimoles) and 210 g (3 moles) of 2,5-dihydrofuran are heated in an autoclave at 190° C. for 5 hours. Unconverted 2,5-dihydrofuran is distilled off. The residue is taken up in methylene chloride and the solution is extracted with 10% strength sodium hydroxide solution. On neutralizing the alkaline solution, crude 4-benzyl-6-isopropyl-1,3-dihydro-furo[3,4-c]pyridin-7-ol is obtained and is extracted with methylene chloride (20.4 g). The product is converted to the hydrochloride by means of dilute hydrochloric acid and the hydrochloride is recrystallized from ethanol; melting point 232°–233° C.

| C, H and N determination (C$_{17}$H$_{20}$ClNO$_2$; 305.5) | | | |
|---|---|---|---|
| Found: | C 66.6% | H 6.6%; | N 4.6% |
| Calculated: | 66.2 | 6.6 | 4.6 |

EXAMPLE 23

4-Benzyl-6-isobutyl-1,3-dihydro-furo[3,4-c]pyridin-7-ol (a) 2-Benzyl-4-isobutyl-5-ethoxyoxazole is prepared by a method similar to Example 11(a). 138 g of N-phenylacetyl-leucine ethyl ester give, after distillation of the product, 63 g of oxazole, boiling point 120°–127°/0.5 mm Hg.

(b) 2-Benzyl-4-isobutyl-5-ethoxyoxazole is reacted with 2,5-dihydrofuran, using the method described in Example 22. 38 g of crude 4-benzyl-6-isobutyl-1,3-dihydro-furo[3,4-c]pyridine-7-ol are obtained. Recrystallization from ethyl acetate gives a pure product, melting point 174°–175° C.

| C, H and N determination (C$_{18}$H$_{21}$NO$_2$; 283) | | | |
|---|---|---|---|
| Found: | C 76.1%; | H 7.5%; | N 5.4% |
| Calculated: | 76.3 | 7.4 | 4.9 |

EXAMPLE 24

4,6-Dibenzyl-1,3-dihydro-furo[3,4-c]pyridin-7-ol (a) 2,4-Dibenzyl-5-ethoxyoxazole is prepared by a method similar to Example 11 (a), starting from N-phenylacetyl-β-phenyl-alanine ethyl ester.

(b) 44 g (150 millimoles) of 2,4-dibenzyl-5-ethoxyoxazole and 210 g (3 moles) of 2,5-dihydrofuran are heated for 8 hours at 180° C. Excess 2,5-dihydrofuran is distilled off and the residue is digested in ether. The undissolved constituent is recrystallized from ethanol. 17.6 g of 4,6-dibenzyl-1,3-dihydro-furo[3,4-c]pyridin-7-ol are obtained, melting point 204°–205° C.

| C, H and N determination (C$_{21}$H$_{19}$NO$_2$; 317) | | | |
|---|---|---|---|
| Found: | C 79.4%; | H 6.2%; | N 4.5% |
| Calculated: | 79.5 | 6.0 | 4.4 |

EXAMPLE 25

4-Benzyl-6-methyl-1,3-dihydro-furo[3,4-c]pyridin-7-ol N-oxide 48.2 g (0.2 mole) of 4-benzyl-6-methyl-1,3-dihydro-furo [3,4-c]pyridin-7-ol in 25 ml of glacial acetic acid are heated with 30 g of acetic anhydride for 2 hours at 100°. The solvent is distilled off under reduced pressure, the residue is taken up in 50 ml of chloroform and 38 g of m-chloroperbenzoic acid are added at 0°. After the mixture has stood for 10 hours at room temperature, the m-chlorobenzoic acid which has precipitated is filtered off. The filtrate is washed with an aqueous sodium bisulfite solution, with dilute sodium carbonate solution and with water, and is dried.

After distilling off the chloroform, the residue is taken up in 100 ml of methanol and 10 g of hydrogen chloride are passed into the solution. On cooling, 50 g of 4-benzyl-6-methyl-1,3-dihydro-furo[3,4-c]pyridin-7-ol N-oxide are obtained. Recrystallization from ethylene glycol monoethyl ether gives the pure N-oxide, melting point 237°–238° C.

| C, H and N determination ($C_{17}H_{17}NO_4$; 299) | | | |
|---|---|---|---|
| Found: | C 70.0%; | H 6.1%; | N 5.3% |
| Calculated: | 70.0 | 5.9 | 5.4 |

EXAMPLE 26

4-α-Phenylethyl-6-methyl-1,3-dihydro-furo[3,4-c]pyridin-7-ol (a) 2-α-Phenylethyl-4-methyl-oxazole is prepared from α-phenylpropionimido-propargyl ester, by a method similar to the preparation of 2-benzyl-4-methyl-oxazole as described in German Laid-Open Application DOS 2,152,367; boiling point 69°–72°/0.2 mm Hg.

(b) 4-α-Phenylethyl-6-methyl-1,3-dihydro-furo[3,4-c]pyridin-7-ol is prepared, using the method described in Example 13, by reacting 2-α-phenylethyl-4-methyloxazole and 3-methylsulfonyl-2,5-dihydrofuran; melting point 163° C.

| C, H and N determination ($C_{16}H_{17}NO_2$; 255) | | | |
|---|---|---|---|
| Found: | C 75.3%; | H 6.6%; | N 5.1% |
| Calculated: | 75.3 | 6.7 | 5.5 |

EXAMPLE 27

4-3'-Trifluoromethylbenzyl-6-methyl-1,3-dihydro-furo[3,4-c]pyridin-7-ol (a) 2-3'-Trifluoromethylbenzyl-4-methyl-oxazole is prepared from propargyl 3-trifluoromethylphenyl-acetate, by a method similar to the preparation of 2-benzyl-4-methyl-oxazole as described in German Laid-Open Application DOS No. 2,152,367; boiling point 70°–72° C./0.1 mm Hg.

(b) 4-3'-Trifluoromethylbenzyl-6-methyl-1,3-dihydro-furo[3,4-c]pyridin-7-ol is prepared, using the method described in Example 13, by reacting 2-3'-trifluoromethylbenzyl-4-methyl-oxazole and 3-methylsulfonyl-2,5-dihydrofuran; melting point 183°–185° C.

| C, H and N determination ($C_{16}H_{14}F_3NO_2$; 302) | | | |
|---|---|---|---|
| Found: | C 63.2%; | H 4.6% | N 4.7% |
| Calculated: | 63.5 | 4.6 | 4.6 |

EXAMPLE 28

4-α-Thenyl-6-methyl-1,3-dihydro-furo[3,4-c]pyridin-7-ol (a) 2-α-Thenyl-4-methyl-oxazole is prepared from propargyl α-thienyl-acetate, by a method similar to the preparation of 2-benzyl-4-methyl-oxazole as described in German Laid-Open Application DOS 2,152,367; boiling point 67°–70° C./0.1 mm Hg.

(b) 4-α-Thenyl-6-methyl-1,3-dihydro-furo[3,4-c]pyridin-7-ol is prepared, using the method described in Example 13, by reacting 2-α-thenyl-4-methyl-oxazole and 3-methylsulfonyl-2,5-dihydrofuran; melting point 216°–218° C.

The formulae which follow illustrate the nomenclature, according to the Ring Index, used for the pyridinols.

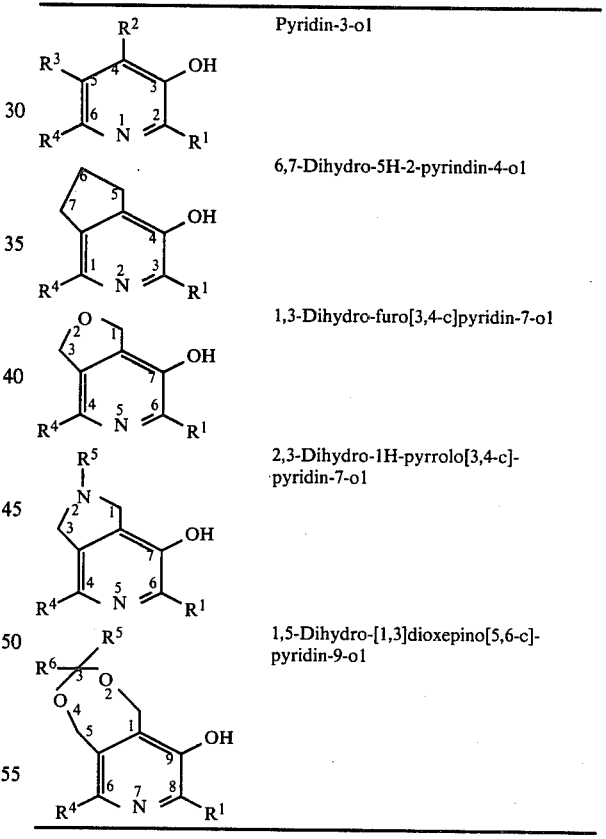

The following are examples of compounds of the formula V which, as such and/or in the form of one of their acid addition salts, have an antiarrhythmic action: 4,6-dibenzyl-1,3-dihydrofuro[3,4-c]pyridin-7-yl 3-dimethylaminopropyl ether, 4-benzyl-6-methyl-1,3-dihydro-furo[3,4-c]pyridin-7-yl 3-isopropylaminopropyl ether, 4-benzyl-6-methyl-1,3-dihydro-furo[3,4-c]pyridin-7-yl 4-isopropylaminobutyl ether, 4-benzyl-6-methyl-1,3-dihydrofuro[3,4-c]pyridin-7-yl 5-isopropylamino-(3-methylpentyl) ether, 4-benzyl-6-methyl-1,3-dihydrofuro[3,4-c]pyridin-7-yl 5-diethylamino-(3-methylpentyl) ether and 4-benzyl-6-methyl-1,3-dihydrofuro[3,4-c]pyridin-7-yl 4-tert.-butylamino-butyl ether.

To determine the anti-arrhythmic activity, the drugs were administered orally to rats (Sprague Dawley strain, weight 180°–240 g) 45 minutes before the start of the narcosis.

The animals were narcotized with thiobutabartital (100 mg/kg administered intraperitoneally). The arrhythmogenic substance used was aconitine, which was administered by intravenous infusion (at a rate of 0.005 mg/kg. min) 60 minutes after administration of the test substance. In the case of untreated animals (N=30), arrhythmias occurred after an average of 3.7±0.9 minutes, the commencement of which can be delayed by anti-arrhythmic agents, the delay depending on the dosage.

For a quantitative evaluation of the linear relation between log dose (mg/kg) of the test substances and the relative prolongation of the duration of aconitine infusion (Δ%), the dose which extended the duration of infusion by 50% (ED 50) was determined. The prior art anti-arrhythmic agent quinidine served as a comparative substance.

The acute toxicity was determined on groups of 10 or 20 female Swiss mice, weighing 20–26 g, the compounds being administered intraperitoneally. The LD 50 was calculated as the dose (Probit analysis) after which 50% of the animals died within 24 hours.

TABLE 1

| | Anti-arrhythmic action and acute toxicity | | | | | | |
|---|---|---|---|---|---|---|---|
| | Anti-arrhythmic action[1] | | | | | Acute | |
| Example | Effective dose | | Maximum action[4] | | | toxicity | Therapeutic |
| No. | ED 50[2] | R.A.[3] | Dose | Δ%[5] | R.M.A.[6] | LD 50 | range[7] |
| III | 14.9 | 2.84 | 215 | 319 | 2.40 | 98.3 | 6.60 |
| IV | 28.9 | 1.46 | 215 | 457 | 3.44 | 139 | 4.81 |
| V | 5.66 | 7.47 | 100 | 358 | 2.69 | 99.3 | 17.54 |
| VI | 12.2 | 3.47 | 100 | 333 | 2.50 | 82.2 | 6.74 |
| VII | 11.3 | 3.74 | 100 | 261 | 1.96 | 88.9 | 7.86 |
| VIII | 9.29 | 4.60 | 46.4 | 298 | 2.24 | 73.9 | 7.95 |
| Quinidine | 42.3 | 1.00 | 215 | 133 | 1.00 | 180 | 4.26 |

[1] Aconitine-induced arrhythmia, rats
[2] Dose (mg/kg), administered orally, which prolongs the duration of aconitine infusion (in minutes) by 50%
[3] R.A. = relative activity; quinidine = 1.00
[4] Action of the highest non-toxic dose
[5] Prolongation of the duration of aconitine infusion, Δ%
[6] R.M.A. = relative maximum activity
[7] $\frac{LD\ 50}{ED\ 50}$ Therapeutic agents and formulations which contain a compound of the formula V as the active ingredient are prepared with conventional carriers or diluents and the conventionally used pharmaceutical auxiliaries in accordance with the desired route of administration, in the conventional manner and with a suitable dosage, the individual doses for man being from 5 to 100 mg.

EXAMPLES OF COMPOUNDS OF THE FORMULA V

EXAMPLE I (a) 12.1 g (50 millimoles) of 4-benzyl-6-methyl-1,3-dihydrofuro[3,4-c]pyridin-7-ol are suspended in 40 ml of dry dimethylsulfoxide and converted to the sodium salt by adding 1.75 g (60 millimoles) of sodium hydride (85% strength) in oil at 20° C. When the evolution of hydrogen has ceased, 8.1 g (75 millimoles) of freshly distilled β-dimethylaminoethyl chloride are added dropwise and the mixture is left to stand for 15 hours at 10° C. The dimethylsulfoxide is distilled off in a high vacuum. The residue is taken up in methylene chloride, the salts and unconverted pyridinol are washed out with dilute sodium hydroxide solution and the methylene chloride phase is dried and concentrated under reduced pressure. The residue is converted to the hydrochloride by means of dilute hydrochloric acid and the hydrochloride is recrystallized from a mixture of ethanol and ether. 10.0 g of 4-benzyl-6-methyl-1,3-dihydro-furo[3,4-c]pyridin-7-yl β-dimethylaminoethyl ether bis-hydrochloride, melting point 213°–214° C., are obtained.

(b) 12.1 g (50 millimoles) of 4-benzyl-6-methyl-1,3-dihydrofuro[3,4-c]pyridin-7-ol are dissolved in 25 ml of 2 N aqueous sodium hydroxide solution. After evaporating off the water, finally under reduced pressure at 100° C., the residue is suspended in 50 ml of tetrahydrofuran to which 5 ml of hexamethylphosphorotriamide have been added. 8.1 g (75 millimoles) of freshly distilled β-dimethylamino-ethyl chloride are added dropwise and the mixture is boiled for 10 hours. After distilling off the tetrahydrofuran the residue is worked up as described under (a). 9.3 g of 4-benzyl-6-methyl-1,3-dihydro-furo[3,4-c]pyridin-7-yl β-dimethylaminoethyl ether bis-hydrochloride, melting point 213°–214° C., are obtained. % N: calculated 7.3%, found 7.3%.

EXAMPLE II 12.1 g (50 millimoles) of 4-benzyl-6-methyl-1,3-dihydrofuro[3,4-c]pyridin-7-ol are converted to the sodium salt as described in Example I (a) and are reacted with 9.2 g (75 millimoles) of N-(3-chloropropyl)-N,N-dimethylamine. Working up as described in Example I gives 16.0 g of 4-benzyl-6-methyl-1,3-dihydro-furo[3,4-c]pyridin-7-yl 3-dimethylaminopropyl ether bishydrochloride, which is recrystallized from isopropanol-ethanol; melting point 202°–204° C. % N: calculated 7.0, found 7.1.

EXAMPLE III

Using the method described in Example II, 4,6-dibenzyl-1,3-dihydro-furo[3,4-c]pyridin-7-ol gives 4,6-dibenzyl-1,3-dihydrofuro[3,4-c]pyridin-7-yl 3-dimethylaminopropyl ether. Melting point of the free base 115° C. % N: calculated 5.9%, found 5.6%.

EXAMPLE IV (a) A mixture of 24.2 g (100 millimoles) of 4-benzyl-6-methyl-1,3-dihydro-furo[3,4-c]pyridin-7-ol, 113 g (1 mole) of 1,3-dichloropropane, 2 g of benzyltriethylammonium chloride, 100 ml of toluene and 100 g of 50% strength sodium hydroxide solution is heated for 3 hours at 90° C., whilst stirring. The organic phase is separated off and washed with 50 ml of water. After stripping off the solvent and the excess 1,3-dichloropropane, 30.7 g of 4-benzyl-6-methyl-1,3-dihydro-furo[3,4-c]pyridin-7-yl 3-chloropropyl ether are obtained; this material contains a small proportion of 1,3-bis-(4-benzyl-6-methyl-1,3-dihydro-furo[3,4-c]pyridin-7-oxy)-propane which does not interfere with the subsequent reaction.

(b) 8.0 g (25 millimoles) of the product obtained as described under (a) are heated with 15 g (250 millimoles) of isopropylamine in an autoclave at 100° C. for 7 hours. The excess amine is distilled off under reduced pressure. The residue is purified by chromatography over silica gel (using ethyl acetate and methanol). The 4-benzyl-6-methyl-1,3-dihydro-furo[3,4-c]pyridin-7-yl 3-isopropylamino-propyl ether obtained is converted, with dilute hydrochloric acid, to the bis-hydrochloride, and the latter is recrystallized from isopropanol; 7.8 g of material, of melting point 162° C., are obtained. % N: calculated 6.8%, found 6.9%.

The compounds listed in the Table which follows were prepared by a similar method; in the case of the higher-boiling amines, i.e., those boiling at above 100°–120° C., the use of an autoclave is superfluous.

EXAMPLES V–VIII

Using the method described in Example IV (a), but carrying out the reaction with 1,4-dichlorobutane, 1,4-dibromo-but-2-ene, 1,5-dichloro-pentane and 1,5-dichloro-3-methyl-pentane instead of 1,3-dichloropropane, the corresponding ω-haloalkyl ethers are prepared, and these are then reacted with an amine, using the method described in Example IV (b), to give the compounds listed in the Table below.

TABLE

| Example | A—NR$^5$R$^6$ | Melting point ° C. | %N Calc. | %N Found |
|---|---|---|---|---|
| V | (CH$_2$)$_4$NHCH(CH$_3$)$_2$ | 198–199 | 6.5 | 6.5 |
| VI | (CH$_2$)$_2$CH(CH$_3$)(CH$_2$)$_2$NH—CH(CH$_3$)$_2$ | 169–170 | 6.2 | 6.2 |
| VII | (CH$_2$)$_2$CH(CH$_3$)CH$_2$)$_2$N(C$_2$H$_5$)$_2$ | 161–162 | 6.0 | 6.0 |
| VIII | (CH$_2$)$_4$NH—C(CH$_3$)$_3$ | 198–199 | 6.3 | 6.4 |

We claim:
1. Pyridin-3-ols of the formula I where R$^1$ is hydrogen, alkyl of 1 to 4 carbon atoms or benzyl, R$^2$ and R$^3$ are identical and each is methyl substituted by hydroxyl, alkoxy, alkylamino or dialkylamino, each with alkyl of 1 to 4 carbon atoms, acetoxy, chlorine or bromine, or R$^2$ and R$^3$ together are trimethylene, 2-oxatrimethylene, 2-azatrimethylene or 2-alkylazatrimethylene with alkyl of 1 to 4 carbon atoms, and R$^4$ is phenyl or benzyl, where phenyl may be unsubstituted or monosubstituted or disubstituted by hydroxyl, methoxy, halogen, e.g. fluorine, chlorine, bromine or iodine, or methyl, and their N-oxides and addition salts with acids.

* * * * *